United States Patent [19]

Raabe et al.

[11] 3,969,363
[45] July 13, 1976

[54] DERIVATIVES OF 1-PHENOXY-3-AMINO-PROPAN-2-OL AND PROCESS FOR THEIR PRODUCTION

[75] Inventors: Thomas Raabe, Rodenbach; Otto Grawinger, Frankfurt am Main; Josef Scholtholt, Mittelbuchen; Rolf-Eberhard Nitz, Bergen-Enkheim; Eckhard Schraven, Frankfurt am Main, all of Germany

[73] Assignee: Cassella Farbwerke Mainkur Aktiengesellschaft, Frankfurt am Main-Fechenheim, Germany

[22] Filed: Dec. 10, 1974

[21] Appl. No.: 531,325

[30] Foreign Application Priority Data
Dec. 12, 1973 Luxemburg............................ 69043

[52] U.S. Cl........................... 260/296 AE; 424/263; 260/240 J; 260/296 R; 260/307 F; 260/348 R; 260/570.5 C
[51] Int. Cl.²........................................ C07D 213/72
[58] Field of Search........ 260/240 J, 296 AE, 296 R

[56] References Cited
UNITED STATES PATENTS

| | | | |
|---|---|---|---|
| 3,328,417 | 6/1967 | McLoughlin et al. | 260/307 |
| 3,412,154 | 11/1968 | Fleming et al. | 260/570.5 |
| 3,679,693 | 7/1972 | Ross et al. | 260/296 AE |
| 3,723,476 | 3/1973 | Nakanishi et al. | 260/347.7 |
| 3,830,806 | 8/1974 | Raabe et al. | 260/240 J |
| 3,862,953 | 1/1975 | Berger et al. | 260/295 T |

*Primary Examiner*—John D. Randolph
*Attorney, Agent, or Firm*—Francis M. Crawford

[57] ABSTRACT

The present invention relates to new pharmacologically valuable derivatives of 1-phenoxy-3-amino-propan-2-ol having the formula

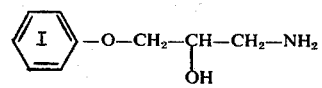

and the aldehyde condensation products and acid addition salts thereof wherein X is selected from the group consisting of

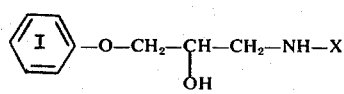

and

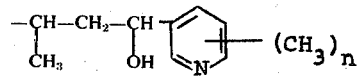

wherein the phenyl ring I may have attached to it up to three similar or different substituents selected from the group consisting of alkyl, alkenyl, alkinyl, cycloalkyl, cycloalkenyl, alkoxy, alkenyloxy, alkinyloxy, benzyloxy, phenyl, halogen and $-NR_1R_2$, wherein $R_1$ is selected from alkyl and acyl, and $R_2$ is selected from hydrogen and alkyl and $n$ is 1, 2 or 3; and to the production thereof by a method selected from (A) reacting 1-phenoxy-3-amino-propan-2-ol having the formula

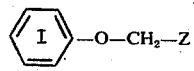

with a compound having the formula Y-X, wherein X has the above defined meaning and Y is selected from halogen, —OH, —OK or —ONa; (B) reacting a compound of the formula

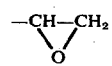

with a compound of the formula $H_2N$—X, wherein X has the above-defined meaning and Z is selected from

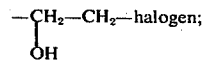

and

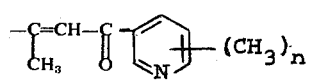

(C) reacting a phenol

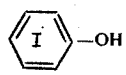

with Z—$CH_2$—NH—X, wherein X and Z have the meaning defined above.

12 Claims, No Drawings

DERIVATIVES OF 1-PHENOXY-3-AMINO-PROPAN-2-OL AND PROCESS FOR THEIR PRODUCTION

The invention relates to new, pharmacologically valuable derivatives of 1-phenoxy-3-aminopropan-2-ol of the general formula I

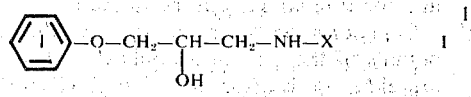

wherein X denotes

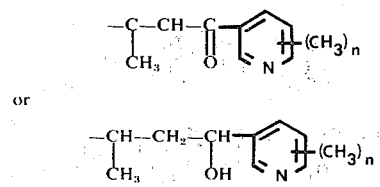

$n$ represents 1, 2 or 3 and the phenyl nucleus I can also be mono-substituted, di-substitued or tri-substituted, particularly by alkyl, alkenyl, alkinyl, cycloalkyl, cycloalkenyl, alkoxy, alkenyloxy, alkinyloxy, benzyloxy, phenyl, halogen or the radical —$NR_1R_2$, $R_1$ representing alkyl or acyl and $R_2$ representing hydrogen or alkyl, to aldehyde condensation products and acid addition salts thereof, and to a process for their preparation. The substituents of the phenyl nucleus I can be identical or different.

Compounds having X =

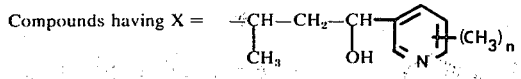

are preferred.

By the compounds of the general formula I, there are also understood, within the scope of the present invention, possible stereoisomers and optically active compounds and mixtures thereof, particularly the racemate.

The substituents of the phenyl nucleus I have, in particular, the following meaning: alkyl having 1 to 4 C atoms, for example methyl, ethyl, propyl or tert.-butyl; alkenyl having up to 6 C atoms, preferably vinyl, allyl, methallyl or crotyl; alkinyl having up to 6 C atoms, for example propargyl; cycloalkyl having a ring size of 5 to 8 C atoms, preferably cyclopentyl and cyclohexyl; cycloalkenyl having a ring size of 5 to 8 C atoms, preferably cyclopentenyl; alkoxy having up to 8 C atoms, or alkenyloxy and alkinyloxy having in each case up to 5 C atoms, preferably methoxy, ethoxy, n-propoxy and i-propoxy, butoxy, n-pentyloxy, n-octyloxy, allyloxy, methallyloxy, propargyloxy or benzyloxy. Halogen: preferably fluorine, chlorine or bromine. Alkyl radicals representing $R_1$ or $R_2$ preferably have 1 to 2 C atoms.

By the acyl radical representing $R_1$ there is understood the aryl-substituted or alkyl-substituted carbonyl radical derived from an aromatic or aliphatic carboxylic acid and having up to 11 C atoms, for example formyl, acetyl, propionyl, butyryl, benzoyl, naphthoyl or phenylacetyl, but preferably acetyl or benzoyl.

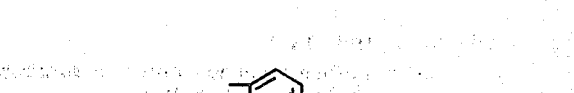

has, in particular, the following meaning: 2-methylpyridyl, 4-methylpyridyl, 6-methylpyridyl, 2,6-dimethylpyridyl, 4,5-dimethylpyridyl, 4,6-dimethylpyridyl, 2,4-dimethylpyridyl and 2,4,6-trimethylpyridyl, The aldehyde condensation products of compounds of the general formula I are oxazolidines of the formula II

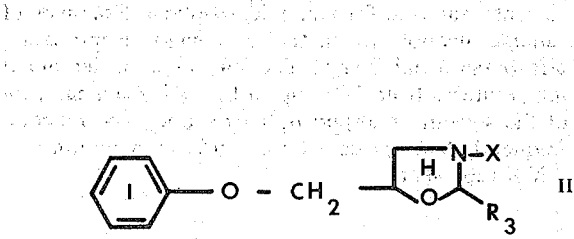

which are formed in the condensation of compounds of the general formula I with an aldehyde of the formula $R_3$ — CHO in which $R_3$ represents hydrogen or a lower alkyl radical having up to 4 C atoms.

Inorganic and organic acids are suitable for the formation of salts with the compounds of the general formula I. Examples of suitable acids are hydrogen chloride, hydrogen bromide, phosphoric acid, sulphuric acid, oxalic acid, lactic acid, tartaric acid, acetic acid, salicylic acid, benzoic acid, citric acid, adipic acid or naphthalene-1,5-disulphonic acid. Pharmaceutically acceptable acid addition salts are preferred.

The phenyl nuclei I of the structural formulae which follow can be subtituted as indicated above in the case of the general formula I.

In order to prepare the compounds of the general formula I, a 1-phenoxy-3-aminoropan-2-ol of the general formula III is reacted with a compound of the general formula IV with elimination of H-Y to form a compound I according to the invention:

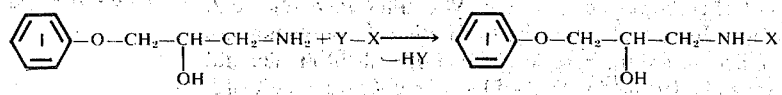

In this, X has the meaning already mentioned and Y denotes halogen, particularly chlorine or bromine, and, if X represents

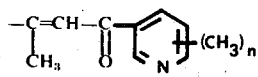

also —OH, —OK or —ONa.

The reaction is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, for example acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N—methylpyrrolidone. The solvents used are, in particular, polar solvents, such as, for example, alcohols. Examples of suitable alcohols are methanol, ethanol, isopropanol, tert.-butanol and the like. The reaction is carried out at temperatures from 20°C up to the reflux temperature of the solvent or dispersing agent used. The reaction frequently takes place even at normal temperature.

If X represents

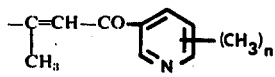

the reaction is accelerated by adding an acid, preferably hydrogen chloride. Examples of other suitable acids are carboxylic acids, such as, for example, formic acid, acetic acid, propionic acid or butyric acid; sulphonic acids, such as, for example, benzenesulphonic acid and p-toluenesulphonic acid; or mineral acids, such as, for example, sulphuric acid and phosphoric acid. If a compound of the general formula IV having Y = OH is employed, even catalytic amounts of the acid, for example of acetic acid or formic acid, are adequate to accelerate the reaction. If compounds of the general formula IV having Y = ONa or OK are employed, about 1 mol of the acid is added. Instead of adding an acid, it is also possible to accelerate the reaction by employing the compound of the general formula III in the form of a salt, for example the hydrohalide. If a compound of the general formula IV in which Y represents halogen is employed, it is also possible to employ this compound of the general formula IV in the form of the hydrohalide. In the preparative process according to the invention, the acid addition salts of the compound I can be formed, or, on adding an acid-binding agent such as potassium carbonate or sodium carbonate, the free amines can be formed.

Depending on the meaning of X, the starting compounds of the general formula IV which are required are either derivatives of 1-(3-pyridyl)-but-2-en-1-one of the general formula V or of 1-(3-pyridyl)-butan-1-ol of the general formula VI:

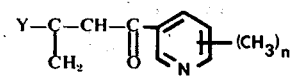 V

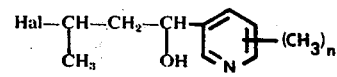 VI

In this, Y has the meaning already indicated and Hal represents halogen, particularly chlorine or bromine. Starting compounds of the general formula V can be obtained, either by reacting a methylnicotinic acid ester, particularly the methyl or ethyl ester, with acetone under the conditions of an alkaline ester condensation, or by reacting an acetic acid ester, particularly methyl or ethyl acetate, under analogous conditions with methyl-3-acetylpyridines. This gives the sodium salt or potassium salt of the formula VII or VIII, respectively:

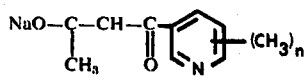  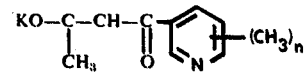

VII  VIII

The free 2-methylnicotinoyl-1-methylvinyl alcohol of the formula IX, which are tautomeric with the methylnicotinoyl-acetone of the formula X:

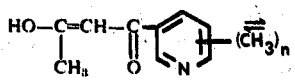  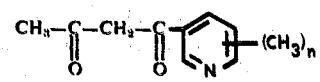

IX  X are obtained from these salts by hydrolysis.

By reacting the compounds of the formula IX or X with suitable halogenating agents, such as, for example, thionyl chloride or phosphorus tribromide, the corresponding 3-halogeno-1-[methyl-3-pyridyl]-but-2-en-1-one of the general formula XI

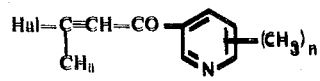 XI wherein Hal represents halogen, particularly chlorine or bromine, is obtained. Compounds of the general formula VI can be prepared from the corresponding compounds of the formula XI by hydrogenation, appropriately by means of complex hydrides, such as, for example, lithium aluminum hydride, sodium borohydride or the like.

The compounds of the general formula III which are required as starting compounds can be prepared by reacting, with ammmonia or with compounds which split off ammonia, a compound of the general formula XII or XIII

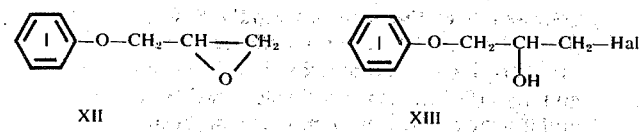

XII            XIII

Hal in XIII denoting a halogen atom, particularly chlorine or bromine, or a mixture of a compound XII with a compound XIII which is identically substituted in the phenyl nucleus I. The reaction can be carried out under atmospheric pressure or under elevated pressure at ambient temperature and can be accelerated or brought to completion by supplying heat, for example by heating to 70°C.

The compounds of the general formula XII and XIII can be prepared by reacting a phenol of the general formula XIV

 XIV with an epihalogenohydrin, appropriately with epichlorohydrin or epibromohydrin. A compound of the general formula XII or XIII or a mixture of compounds of the general formula XII and XIII is formed in the course thereof, depending on the reaction conditions. The reaction product formed can be isolated before being further reacted with ammonia, but it can also be directly reacted further without isolation.

Compounds of the general formula I can also be prepared by reacting a compound of the general formula XV with a compound of the general formula XVI:

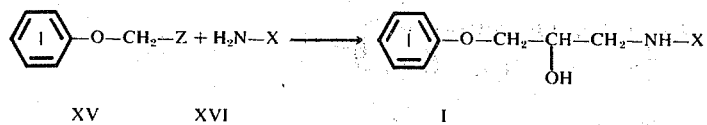

XV           XVI                    I

In this, X has the meaning already mentioned and Z denotes:

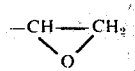

or

—CH—CH$_2$—Hal
 |
 OH wherein Hal represents a halogen atom, particularly chlorine or bromine.

The reaction is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, such as, for example acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. The solvents used are, in particular, polar solvents, such as, for example alcohols. Examples of suitable alcohols are methanol, ethanol, isopropanol, tert.-butanol and the like. The reaction is carried out at tempertures from 20°C up to the reflux temperature of the solvent or dispersing agent used. The reaction frequently takes place at temperatures of 40° to 50°C.

It can be advisable to employ the starting compound of the formula XVI in a one- to 10-fold molar excess and/or to add the reaction component of the general formula XV in a dissolved or suspended form to the dissolved or suspended reaction component of the general formula XVI. The molar ratio between the compounds of the general formula XV and XVI can be 1 : 1 to 1 : 10 and optionally even more.

In carrying out the reaction, a compound of the general formula XII or of the general formula XIII or a mixture of both these compounds, can be employed as the compound of the general formula XV.

If a compound of the general formula XIII is present, it is also possible to carry out the reaction in the presence of acid-binding agents, such as potassium carbonate, sodium carbonate and the like. Without an acid-binding agent, the hydrohalides of the compounds of the general formula I are usually obtained.

The preparation of the starting compounds of the general formula XVI is described in the examples.

In order to prepare the compounds of the general formula I it is also possible to react a phenol of the general formula XIV with a compound of the general formula XVII to give a compound of the general formula I:

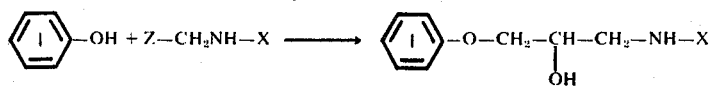

In this, X has the meaning already mentioned and Z denotes:

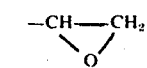

or

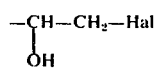

wherein Hal represents a halogen atom, particularly chlorine or bromine.

This reaction too is normally carried out in a suitable solvent or dispersing agent in which the reactants are dissolved or suspended. Examples of solvents or dispersing agents of this kind are aromatic hydrocarbons, such as, for example, benzene, toluene or xylene; ketones, such as, for example, acetone or methyl ethyl ketone; halogenated hydrocarbons, such as, for example, chloroform, carbon tetrachloride, chlorobenzene or methylene chloride; ethers, such as, for example, tetrahydrofurane and dioxane; sulphoxides, such as, for example, dimethylsulphoxide; or tertiary acid amides, such as, for example, dimethylformamide and N-methylpyrrolidone. Polar solvents, in particular, such as, for example, alcohols, are used as the solvent. Examples of suitable alcohols are methanol, ethanol, isopropanol, tert.-butanol and the like. If Z denotes

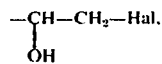

the reaction is generally carried out in the presence of an acid-binding agent, such as, for example, potassium carbonate, sodium carbonate or sodium bicarbonate. The reaction can also be carried out in aqueous alkalis, such as, for example, dilute sodium hydroxide or potassium hydroxide solution. The reaction temperature can be from 20° up to the reflux temperature of the solvent or dispersing agent used.

It can be advisable to employ the starting compound of the general formula XVII in a one- to 10-fold molar excess and/or to add the reaction component of the general formula XIV in a dissolved or suspended form to the dissolved or suspended reaction component of the general formula XVII. The molar ratio between the compounds of the general formula XIV and XVII can be 1 : 1 to 1 : 10 and optionally even more.

In carrying out the reaction it is possible to employ a compound of the general formula XVIII or of the general formula XIX or a mixture of both these compounds, as the compound of the general formula XVII.

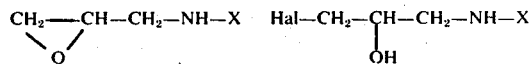

XVIII                    XIX

The compounds of the general formula XVIII and XIX can be prepared by reacting a compound of the general formula XVI with an epihalogenohydrin, appropriately with epichlorohydrin or epibromohydrin. A compound of the general formula XVIII or XIX or a mixture of compounds of the general formula XVIII and XIX is formed in the course thereof, depending on the reaction conditions. The reaction product formed can be isolated in order to be reacted further, but it can also be directly reacted without isolation.

The compounds of the general formula I in which X denotes the radical

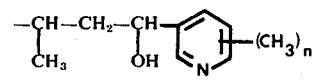

and which therefore have the general formula XX

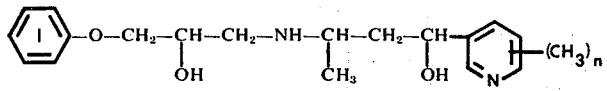 XX can also be prepared by hydrogenating a compound of the general formula XXI, XXII or XXIII

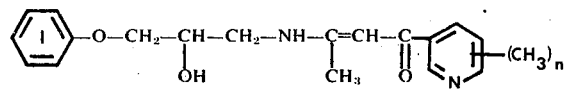 XXI

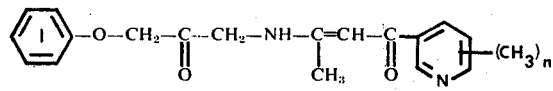 XXII

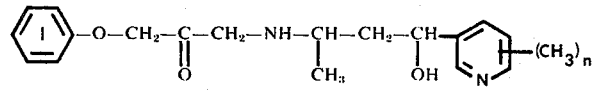 XXIII

It is advantageous to employ, for the hydrogenation, complex hydrides, such as, for example, lithium aluminium hydride, sodium borohydride and the like. The reaction is carried out under the reaction conditions which are known for these hydrides, normally in alcohol or an alcohol/water mixture at room temperature or elevated temperature, for example while boiling under reflux. In some cases the hydrogenation can also be carried out catalytically, for example using a palladium-charcoal catalyst.

The starting compounds of the general formula XXI are compounds, according to the invention, of the general formula I wherein X represents the radical a dehydrating agent, such as anhydrous potassium carbonate.

The acid addition salts of the compounds of the general formula I can be prepared from the components in a manner which is in itself known. The use of a diluent is generally advantageous here, the di-salts of the compounds of the general formula I being generally obtained when there is an excess of acid. The mono-acid addition salts are obtained either by controlled addition of only 1 mol of acid or by partial hydrolysis of the di-acid addition salts.

The compounds of the general formula I, their aldehyde condensation products II and their pharmaceuti-

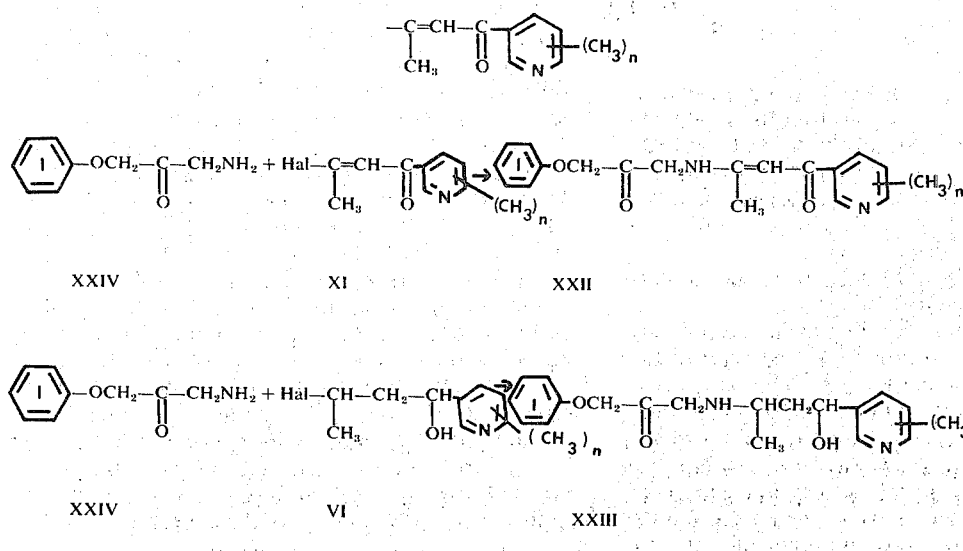

The reaction between the compounds of the general formula XXIV and XI or XXIV and VI, respectively, is carried out in solvents such as benzene, toluene, chloroform, methylene chloride, dioxane and the like, at normal temperature or elevated temperature in the presence of at least molar quantities of an acid-binding agent, such as potassium carbonate or sodium carbonate, or in the absence of acid-binding agents, the hydrohalides of the compounds XXII or XXIII being usually obtained in the latter case.

Compounds of the general formula XXIV can be prepared, for example, by gentle oxidation of the aminopropanols III cally acceptable acid addition salts possess valuable pharmaceutical properties. Thus they are suitable for example, for the treatment or prophylaxis of heart diseases. In addition, some of them have very marked β-adrenolytic or anti-arrhythmic properties. The compounds can, therefore, be used as pharmaceutical preparations, on their own, in mixtures with one another or mixed with diluents or excipients which are pharmaceutically unobjectionable. The pharmaceutical preparations can be present in the form of, for example, tablets, capsules, aqueous or oily solutions or suspensions, emulsions, injectable aqueous or oily solutions or suspensions, dispersible powders or aerosol mixtures.

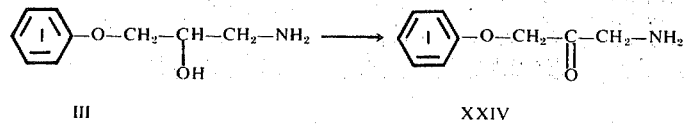

Aldehyde condensation products of the formula II are obtained by reacting, in a diluent or solvent, for example ethanol, preferably in the presence of an acid catalyst, for example acetic acid or hydrochloric acid, and preferably at elevated temperature, compounds of the general formula I with an aldehyde of the formula $R_3$—CHO wherein $R_3$ denotes hydrogen or a lower alkyl radical. The water formed in the reaction can be removed by azeotropic distillation with the aid of an entraining agent, for example benzene, or by means of Besides the compounds of the general formula I, the pharmaceutical preparations can also contain one or more other pharmaceutically active substances, for example sedatives, such as, for example, Luminal, Meprobamat and Chlorpromazine; vasodilators, such as, for example, glycerol trinitrate and carbochromene, diuretics, such as, for example, chlorothiazide; agents for tonicising the heart, such as, for example, digitalis preparations; hypotension agents, such as, for example, Rauwolfia alkaloids; and broncho-dilators and sympathomimetic agents, such as, for example, Isoprenalin and Ephedrin.

Compounds according to the invention, of the general formula I, which are preferred are those in which X has the meaning:

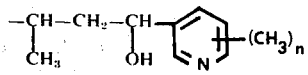

Compounds of the formula

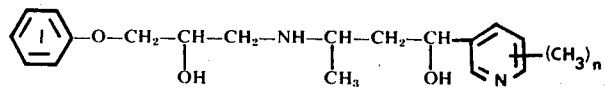

wherein the nucleus I is selected from the group consisting of phenyl, chlorophenyl, bromophenyl, alkoxyphenyl having 1 to 8 carbon atoms in the alkoxy moiety, allyloxyphenyl, methallyloxyphenyl, benzyloxyphenyl, acetaminophenyl,
n is 1, 2 or 3,
and their pharmaceutically acceptable acid addition salts are particularly preferred.

The blocking action of the compounds according to the invention on the β1-receptors of the heart and on the β2-receptors of the cardiovascular system was investigated as follows: the blood pressure in the left-hand ventricle was measured on mongrel dogs of both sexes under anaesthesia by Chloralose-urethane-morphine and the pressure signal was continuously differentiated by means of an analogue computer (BRUSH Instruments, Cleveland/Ohio) and, inter alia, the rate of pressure increase (Dp/dt) was recorded. In addition, the perfusion of a femoral artery was measured by means of an electromagnetic flow meter (Model M4000 of Messrs. Statham) and the perfusion was recorded in ml/minutes.

Alterations in the maximum rate of pressure increase (Dp/dt max.) compared with the zero value were induced by intravenous administration of Isoproterenol (0.5 gamma/kg), a known sympathicomimetic agent (β1-reaction), while alterations of the peripheral perfusion, compared with the zero value, were induced by intra-arterial administration of Isoproterenol (0.05 gamma/kg) (β2-reaction) (D. DUNLOP and R. G. Shanks: Selective blockade of adrenoceptive beta-receptors in the heart. Brit. J. Pharmac. Chemother. (1968) 32, 201–218).

The substances to be tested for β-receptor blocking were administered intravenously in increasing dosages to the animals, which had been anaesthetised and stimulated by means of Isoproterenol, and the quantity of substance was determined at which a 50 % inhibition of the two reactions caused by Isoproterenol occurred (ED50). The ED50 values of the β1-receptor inhibition (mg/kg intravenous) and the ED50 values of the β2-receptor inhibition (mg/kg intravenous) are given in the table which follows. In addition, the relative ED 50 values were calculated for both cases, taking as a basis 4-(2-hydroxy-3-isopropylaminopropoxy)-acetanilide, which was employed as a reference substance, the ED 50 values of the latter being made equivalent to 100. The quotient derived from the ED 50 of the β2-receptor inhibition and the ED 50 of the β1-receptor inhibition represents a measure of the cardioselective action of the substances under investigation. The higher this quotient is, the better the cardioselective action. If the quotient of the reference substance 4-(2-hydroxy-3-isopropylamino-propoxy)-acetanilide is made equivalent to 1, the relative factor indicates how much better the cardioselective action of the compound according to the invention is than that of the reference substance.

Furthermore, the relative ED 50 values of the β1-receptor inhibition (column 2 of the table which follows) are a measure of the effectiveness of the substances to be tested. The lower the figures are, the more active the substances, that is to say the smaller the quantity required for the production of the therapeutic effect.

4-(2-Hydroxy-3-isopropylamino-propoxy)-acetanilide, which is employed as the reference substance, is a preparation which is commercially available as β-blocker and which carries the international unprotected trade name "Practolol".

| Substrate under investigation | β1-receptor inhibition ED 50 (mg/kg intravenous) | Relative β1-receptor inhibition (reference substance = 100) | β2-receptor inhibition ED 50 (mg/kg intravenous) | Relative β2-receptor inhibition (reference substance = 100) | Quotient | ED 50 β2-receptor inhibition / ED 50 β1-receptor inhibition | Quotient, on basis of reference substance = 1 |
|---|---|---|---|---|---|---|---|
| 1-(4-n-Propoxy-phenoxy)-3-(1-[6-methyl-pyridyl-3]-1-hydroxy-butyl-(3)-amino)-propan-2-ol | 0.011 | 4.6 | 1.80 | 6.8 | | 171 | 1.5 |
| 1-(4-Bromo-phenoxy)-3-(1-[6-methyl-pyridyl-3]-1-hydroxy-butyl-(3)-amino)-propan-2-ol | 0.074 | 31.1 | — | | | — | |
| 1-(4n-Butoxy-phenoxy)-3-(1-[6-methyl-pyridyl-3]-1-hydroxy-butyl-(3)-amino)-propan-2-ol | 0.067 | 28.2 | 32.66 | 123.2 | | 487 | 4.4 |
| 1-(4-n-Pentyloxy-phenoxy)-3-(1-[6-methyl-pyridyl-3]-1-hydroxy-butyl-(3)-amino)-propan-2-ol | 0.057 | 29.9 | 7.74 | 29.2 | | 136 | 1.2 |
| 1-(p-Acetamino-phenoxy)-3-(1-[6-methyl-pyridyl-3]-1-hydroxy-butyl-(3)-amino)-propan-2-ol (as L-(+)-tartrate) | 0.012 | 5.04 | 1.99 | 7.5 | | 165 | 1.5 |
| Reference substance: 4-(2-Hydroxy-3-isopropyl- | | | | | | | |

| Substrate under investigation | β1-receptor inhibition ED 50 (mg/kg intravenous) | Relative β1-receptor inhibition (reference substance = 100) | β2-receptor inhibition ED 50 (mg/kg intravenous) | Relative β2-receptor inhibition (reference substance = 100) | Quotient: ED 50 β2-receptor inhibition / ED 50 β1-receptor inhibition | Quotient, on basis of reference substance = 1 |
|---|---|---|---|---|---|---|
| amino-propoxy)-acetanilide | 0.238 | 100 | 26.505 | 100 | 110 | 1 |

A tablet containing a compound according to the invention and having a total weight of 100 mg, can have the following composition, for example:

5 mg of 1-(4-n-propoxyphenoxy)-3-(1-[6-methyl-pyridyl-3]-1-hydroxy-butyl(3)-amino)-propan-2-ol
10 mg of colloidal silicic acid (Aerosil)
72.5 mg of DAB7 lactose
1.5 mg of gelatine
8.5 mg of DAB7 maize starch and
2.5 mg of Mg stearate USPXVIII Depending on the severity of the case to be treated, it is possible, for example, to administer 1 to 2 of these tablets to a patient three times daily.

The preparation of the compounds of the general formula I is illustrated in greater detail in the following examples. The compounds are frequently oils which cannot be distilled, so that in some cases no melting point is shown. However, in all cases the structure indicated has been checked by molecular analysis and/or the infrared spectrum or nuclear resonance spectrum.

EXAMPLE 1

5.2 g of 1-(o-allyloxyphenoxy)-3-amino-propan-2-ol hydrochloride

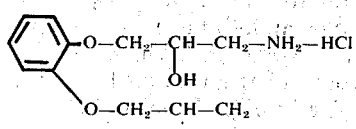

are suspended in 70 ml of ethanol, 4.3 g of the potassium salt of 4-methylnicotinoyl-acetone

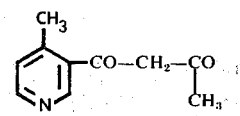

are then added and the mixture is stirred at room temperature for 24 hours and finally heated under reflux for 2 hours. The suspension is filtered and the residue is washed with ethanol. The filtrate, including the alcohol washings, is concentrated in vacuo. This leaves an oily residue which becomes solid after a short time. The solidified oil, together with the residue left from the alcohol washings, is triturated several times with water and is then recrystallised from ethanol. This gives 1-[2-(4-methylnicotinoyl)-1-methyl-vinylamino]-3-(o-allyloxyphenoxy)-propan-2-ol of the formula

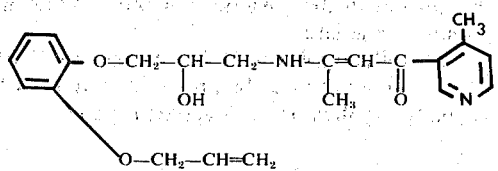

Melting point: 111°C
Analysis: ($C_{22}H_{26}N_2O_4$)
Calculated: C 69.1 H 6.8 N 7.3
Found: C 69.3 H 6.6 N 7.1
Yield: 69% of theory The 4-methylnicotinoyl-acetone required can, inter alia, be prepared as follows: 6.5 g of 4-methylnicotinic acid ethyl ester [prepared from 3-cyano-4-methylpyridine by means of concentrated sulphuric acid and absolute ethanol in an autoclave in a manner analogous to the instructions of J. M. Bobbitt and D. A. Scola, J. Org. Chem. 25, 560 (1960)]

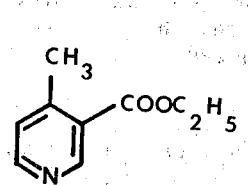

are dissolved in 50 ml of absolute xylene, 4.5 g of potassium tert.-butylate are added and 6.1 g of anhydrous acetone are then added dropwise at 45°C. The mixture is subsequently stirred for 1 hour at 45°C and then heated under reflux for 2 hours. The ethanol formed and the residual acetone are then distilled off, water is added to the xylene solution, the water phase is separated off and the xylene phase is washed twice more with water. The combined aqueous phases are then adjusted to pH 4 by means of glacial acetic acid and are finally brought to pH 5 by means of sodium bicarbonate. A precipitate separates out at this pH value and is recrystallised once from water.

This gives 4-methylnicotinoyl-acetone

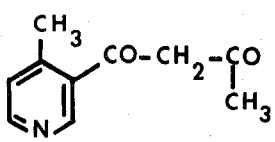

of melting point: 70°C.
Analysis: ($C_{10}H_{11}NO_2$)
Calculated: C 67.8 H 6.2 N 7.9
Found: C 67.9 H 6.5 N 8.0

4-Methylnicotinoyl-acetone can be converted into its potassium salt in the customary manner by means of potassium alcoholate.

The 1-(o-allyloxyphenoxy)-3-amino-propan-2-ol hydrochloride required can be prepared as follows: 60 g of 1-(o-allyloxyphenoxy)-2,3-epoxypropane

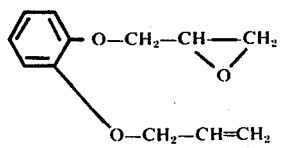

(prepared from o-allyloxyphenol and epichlorohydrin in the presence of potassium carbonate in acetone) are dissolved in 600 ml of methanol, 300 ml of liquid ammonia are added and the mixture is stirred for 3 hours in an autoclave at 70°C. It is then concentrated, and the residue is dissolved in benzene and extracted twice with dilute hydrochloric acid, and the aqueous acid phase is separated off, rendered alkaline and extracted three times with benzene and the combined benzene phases are concentrated. The solid residue is recrystallised once from benzene. This gives 1-(o-allyloxyphenoxy)-3-amino-propan-2-ol

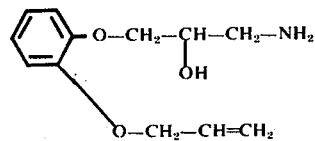

in a yield of 67% of theory.
Melting point: 89°C.

The base can be converted in the customary manner by means of ethereal hydrochloric acid into 1-(o-allyloxyphenoxy)-3-amino-propan-2-ol hydrochloride of melting point 110°C.

EXAMPLE 2

7.1 g of 6-methylnicotinoyl-acetone

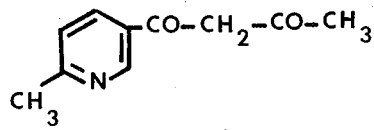

9.3 g of racemic 1-(o-ethoxy-phenoxy)-3-amino-propan-2-ol

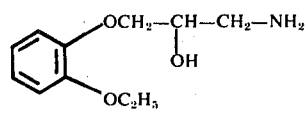

and 60 ml of ethanol are stirred for 20 hours at room temperature. The solution is evaporated in vacuo and the residue is recrystallised from toluene. This gives 12.6 g of racemic 1-[2-(6-methylnicotinoyl)-1-methyl-vinylamino]-3-(o-ethoxyphenoxy)-propan-2-ol of the formula

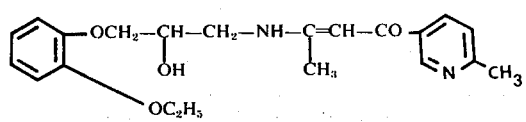

Melting point: 99.5° – 101°C
Analysis: ($C_{21}H_{26}N_2O_4$)
Calculated: C 68.1 H 7.1 N 7.5 O 17.3
Found: C 68.0 H 7.0 N 7.5 O 17.5

The 6-methylnicotinoyl-acetone used as the starting substance can be obtained as follows: 270 g of 5-acetyl-2-methylpyridine (prepared according to Angew. Ch. 67, page 398 from 1-methoxy-but-1-en-3-one and 1-amino-but-1-en-3-one), 5 l of anhydrous toluene, 387 g of ethyl acetate and 537 g of potassium tert.-butylate are stirred for 20 hours at 40° and the mixture is then decomposed by means of a mixture of 3 l of ice water and 288 ml of acetic acid. The phases are separated and the toluene solution is worked up in the customary manner to give 283.5 g of 6-methylnicotinoyl-acetone, boiling point 108°–117°/0.2 mm Hg, which rapidly crystallises throughout and, after recrystallisation from ligroin,, melts at 57°–58°C,

EXAMPLE 3

10.0 g of racemic 1-[2-(6-methyl-nicotinoyl)-1-methylvinylamino]-3-(o-ethoxy-phenoxy)-propan-2-ol

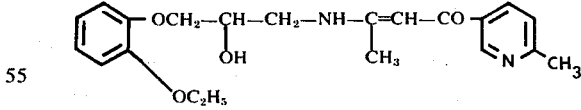

are introduced, at room temperature, into a solution of 90 ml of ethanol and 30 ml of water and 3.0 g of sodium boranate, and the mixture is heated at 70° for 3 hours. After adding a further 1.0 g of sodium boranate and further heating for 2 hours (70°), the solvent is distilled off under reduced pressure and the residue is taken up in water and ethylene chloride. The ethylene chloride solution is thoroughly stirred with dilute hydrochloric acid, the aqueous solution (pH 2–3) is filtered with the aid of a little active charcoal and adjusted to pH 10–11 by means of alkali metal hydroxide solution and the base, which has precipitated as an oil, is taken up in dichloromethane. Drying by means of potassium carbonate and evaporating the solvent up to 60°/0.3 mm Hg gives, as residue, 8.7 g of racemic 1-(o-ethoxy-phenoxy)-3-(1-[6-methyl-pyridyl-3]-1-hydroxy-butyl-3-amino)-propan-2-ol

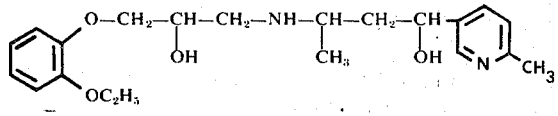

as a viscous oil.
Analysis: ($C_{21}H_{30}N_2O_4$)
Calculated: C 67.3 H 8.1 N 7.5 O 17.1
Found: C 67.0 H 8.1 N 7.3 O 17.5

EXAMPLE 4

If, instead of the racemic 1-(o-ethoxy-phenoxy)-3-amino-propan-2-ol, the laevorotatory isomer thereof

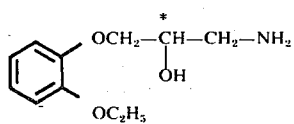

is treated in the same way as described in Example 2, laevorotatory (−)-1-[2-(6-methylnicotinoyl)-1-methyl-vinylamino]-3-(o-ethoxy-phenoxy)-propan-2-ol

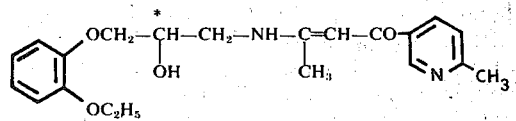

is obtained.
Melting point: 108°–109°, $\alpha_D^{25}$: −52°
Analysis: ($C_{21}H_{26}N_2O_4$)
Calculated: C 68.1 H 7.1 N 7.5 O 17.3
Found: C 67.9 H 7.1 N 7.4 O 17.4
(−)-1-(o-Ethoxy-phenoxy)-3-(1-[6-methylpyridyl-3]-1-hydroxy-butyl-3-amino)-propan-2-ol is obtained from this by reduction in the same way as described in Example 3, as a viscous oil, $\alpha_D^{25}$ = −2.8°.
Analysis: ($C_{21}H_{30}N_2O_4$)
Calculated: C 67.3 H 8.1 N 7.5 O 17.1
Found: C 67.1 H 8.2 N 7.3 O 17.4

Laevorotatory 1-(o-ethoxy-phenoxy)-3-amino-propan-2-ol, which is used as the starting substance, can be prepared as follows from the racemate: 20 g of 1-(o-ethoxy-phenoxy)-3-amino-propan-2-ol (racemate) are dissolved in 295 ml of isopropanol and a solution of 7.1 g of L (+)-tartaric acid in 100 ml of isopropanol is added, whereupon a voluminous, white precipitate separates out. The white product is filtered off, washed well with isopropanol and dried in vacuo. This gives 26.7 g of tartrate (95% of theory) of 1-amino-3-(o-ethoxy-phenoxy)-propan-2-ol, having an optical rotation of +12°.

These 26.7 g are recrystallised three times from a mixture of 40 parts of dimethylformamide and 10 parts of water. This finally gives the laevorotatory tartrate of 1-amino-3-(o-ethoxy-phenoxy)-propan-2-ol (2 mols of amine per 1 mol of tartaric acid), having an optical rotation of −1° (melting point: 201°C). 4 g of the salt, finely powdered, are suspended in 60 ml of dioxane and $NH_3$ gas is passed in for one-half hour at room temperature (the heat of reaction being removed by cooling). The ammonium tartrate is filtered off and the dioxane filtrate is concentrated in vacuo. The solid, white residue is recrystallised from ligroin. This gives laevorotatory (−)-1-amino-3-(o-ethoxy-phenoxy)-propan-2-ol of melting point 87°C.

Yield = 2.6 g = 88% of theory (calculated on the laevorotatory tartrate), optical rotation = −5°.

The following compounds were prepared in accordance with the instructions of Examples 1 to 4:

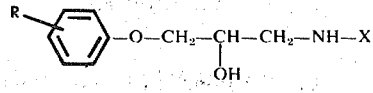

| R | X | |
|---|---|---|
| 2-Cl | —C(CH₃)=CH—CO—(6-methylpyridyl-2) | Melting point 156°–157° |
| 2-Cl | —CH(CH₃)—CH₂—CH(OH)—(6-methylpyridyl-2) | Oil |
| 4-OC₂H₅ | —C(CH₃)=CH—CO—(6-methylpyridyl-2) | Melting point 148°–149° |

-continued
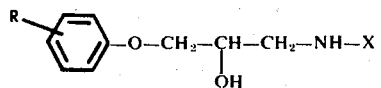
| R | X | |
|---|---|---|
| 2-O—CH₂—CH=CH₂ | 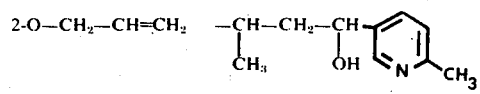 | Oil |
| 4-OC₂H₅ | 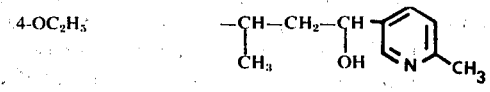 | Oil |
| 4-OC₈H₁₇(n) | 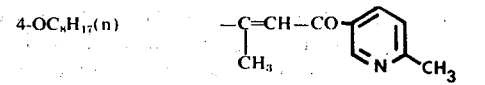 | Melting point 111°–112° |
| 4-OC₈H₁₇(n) | 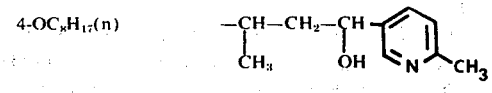 | Melting point 57°–62° |
| 4-OC₃H₇(n) | 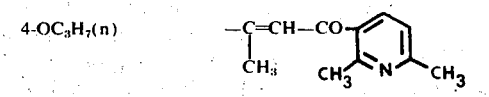 | Melting point 116°–117° |
| 4-OC₃H₇(n) | 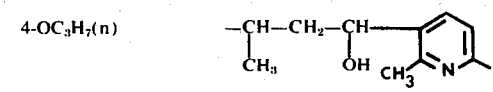 | Oil |
| 4-Br | 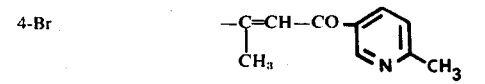 | Melting point 166°–167° |
| 4-Br | 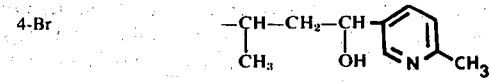 | Oil |
| 4-OC₃H₇(n) | 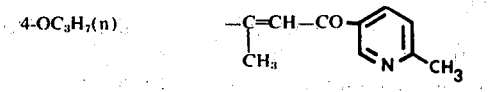 | Melting point 112°–114° |
| 4-OC₃H₇(n) | 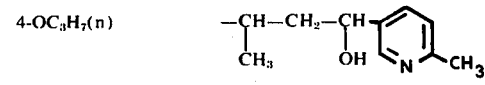 | Oil |
| 4-OCH₃ | 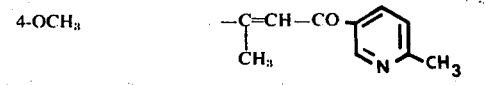 | Melting point 128°–129° |
| 4-OCH₃ | 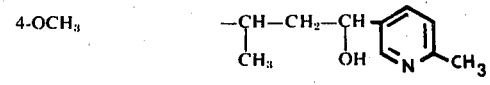 | Oil |
| 4-OC₃H₇(n) | 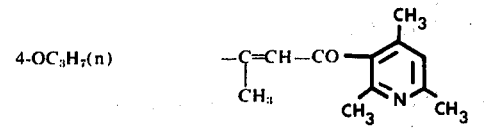 | Melting point 130°–131° |

-continued
R—⌬—O—CH₂—CH—CH₂—NH—X
                |
                OH
| R | X | |
|---|---|---|
| 4-OC₃H₇(n) | 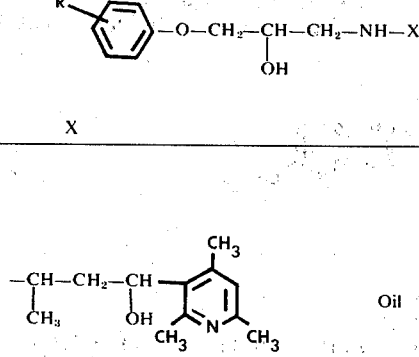 | Oil |
| 4-OCH₂ | 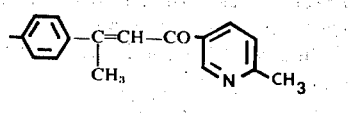 | Melting point 142°–143° |
| 4-OCH₂ | 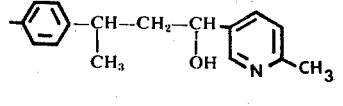 | Oil |
| 4-OC₄H₉(n) | 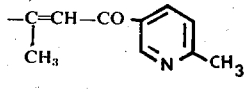 | Melting point 129°–130° |
| 4-OC₄H₉(n) | 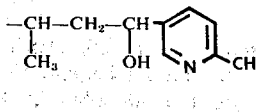 | Oil |
| 4-OC₄H₉(n) | 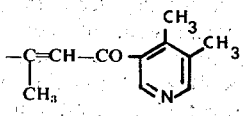 | Melting point 99°–100° |
| 4-OC₄H₉(n) | 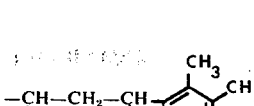 | Oil |
| 4-NHCOCH₃ | 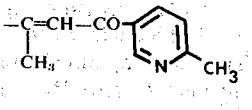 | Melting point 190.5°–191.5° |
| 4-NHCOCH₃ | 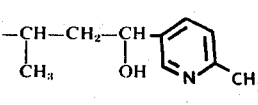 | Oil; salt with 1/2 mol of L-(+)-tartaric acid: Melting point 66°–69° (=neutral L-(+)-tartrate) |
| 4-OC₅H₁₁(n) | 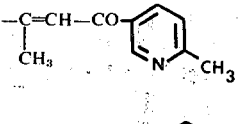 | Melting point 137°–138° |
| 4-OC₅H₁₁(n) | 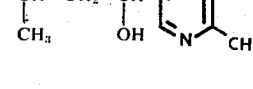 | Oil |

EXAMPLE 5

2.0 g of 1-(4-n-octyloxy-phenoxy)-3-(1-[6-methyl-pyridyl-3]-1-hydroxy-butyl-3-(amino)-propan-2-ol

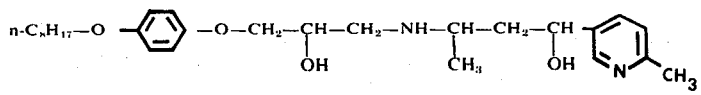

20 ml of ethyl alcohol and 0.45 ml of a 39% strength aqueous formaldehyde solution are heated under reflux for 4 hours. The reaction mixture is evaporated and the residue is taken up in 200 ml of ligroin. After clarifying the ligroin solution by means of a little active charcoal, evaporation gives 1.9 g of 3-(1-hydroxy-1-[6-methyl-pyridyl-3]-butyl-3)-5-(4-n-octyloxy-phenoxymethyl)-oxazolidine

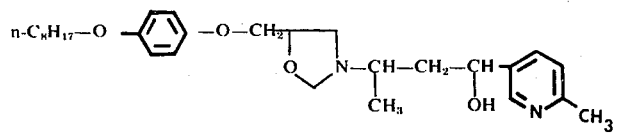

as a colourless oil.

Analysis: ($C_{28}H_{42}N_2O_4$)
Calculated: C 71.5 H 9.0 N 5.9 O 13.6
Found: C 71.7 H 8.9 N 5.8 O 13.7

Preparation of further starting products

Further starting products can be prepared by known methods, for example according to the instructions of Example 1. This gives, for example:

| | |
|---|---|
| 1-(4-n-Propoxy-phenoxy)-2,3-epoxy-propane | melting point: 43°–45° |
| 1-(4-n-Propoxy-phenoxy)-3-amino-propan-2-ol | melting point: 99°–101° |
| 1-(4-n-Octyloxy-phenoxy)-2,3-epoxy-propane | melting point: 46°–48° |
| 1-(4-n-Octyloxy-phenoxy)-3-amino-propan-2-ol | melting point: 106°–107° |
| 1-(4-n-Benzyloxy-phenoxy)-2,3-epoxy-propane | melting point: 55° |
| 1-(4-n-Benzyloxy-phenoxy)-3-amino-propan-2-ol | melting point: 143°–145° |
| 1-(4-n-Amyloxy-phenoxy)-2,3-epoxy-propane | melting point: 37°–38° |
| 1-(4-n-Amyloxy-phenoxy)-3-amino-propan-2-ol | melting point: 101°–103° |

Preparation of starting diketones:

EXAMPLE A 2.5 l of anhydrous toluene, 89.0 g of 3-acetyl-2,6-lutidine, 109.0 g of ethyl acetate and 158 g of potassium tert.-butylate are heated at 60° for 1 hour under nitrogen. The reaction mixture is poured into ½ l of ice water and 81 ml of acetic acid, the phases are separated and, by working up the toluene layer in the customary manner, 107.9 g of 2,6-dimethylnicotinoyl-acetone

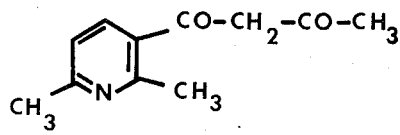

are obtained as a yellowish oil, boiling point 100°–104°/0.1 mm Hg.

The 3-acetyl-2,6-lutidine used as the starting substance can be obtained as follows: 28.5 ml of glacial acetic acid are added slowly to a mixture of 101.0 g of 2-amino-n-pent-2-en-4-one, 139.0 g of 1,1-dimethoxy-butan-3-one and 15.4 g of ammonium acetate, and the mixture is heated at 80° for 20 hours. It is diluted with 300 ml of water and acidified with excess 50% strength sulphuric acid and small quantities of readily volatile substances are steam-distilled off. After cooling, acetyl-lutidine is precipitated from the clear aqueous acid solution by means of alkali metal hydroxide solution, and is taken up in ether and isolated in the customary manner. This gives 90.5 g of 3-acetyl-2,6-lutidine as an oil, boiling point 126°–128°/28 mm Hg.

EXAMPLE B

A mixture of 172.0 g of 3-acetyl-collidine, 4.5 l of anhydrous toluene, 195 g of ethyl acetate and 282.5 g of potassium tert.-butylate is heated at 100° for 4 hours under nitrogen. The reaction mixture is cooled and poured into ½ l of ice water and 140 ml of acetic acid, and the phases are separated and worked up in the customary manner to give 186.1 g of 2,4,6-trimethyl-nicotinoyl-acetone

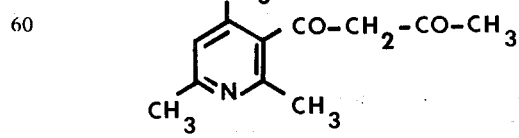

as an oil, boiling point 98°–107°/0.2 mm Hg.

EXAMPLE C

A solution of methylmagnesium iodide (prepared from 18.0 g of magnesium filings, 600 ml of anhydrous diethyl ether and 113.0 g of methyl iodide) is run dropwise, in a stream of nitrogen and at 20°–30°, into a mixture of 79.3 g of 4,5-dimethylnicotinic acid nitrile and 400 ml of 1,2-dimethoxy-ethane. The mixture is heated to 80° while distilling off the diethyl ether and is stirred at this temperature for 1 hour. It is poured into ice and excess hydrochloric acid, the whole is extracted with ether and the clear aqueous acid solution is rendered alkaline by means of aqueous ammonia. Extraction with ether and working up in the customary manner gives 28.3 g of 3-acetyl-4,5-lutidine as an oil, boiling point 74°–80°/0.1 mm Hg.

The 4,5-dimethylnicotinic acid nitrile used as the starting substance can be obtained from α-methylacetoacetic acid ethyl ester. The following are obtained in this way in good yields:

5-Cyano-6-hydroxy-3,4-dimethylpyridone(2) melting point 279°–280°

5-Cyano-2,6-dichloro-3,4-lutidine melting point 77°–79°

4,5-Dimethylnicotinic acid nitrile oil, boiling point 86°–89°/0.2 mm Hg

If 3-acetyl-4,5-lutidine is reacted with ethyl acetate in the same way as described in Example 7, 4,5-dimethyl-nicotinoyl-acetone

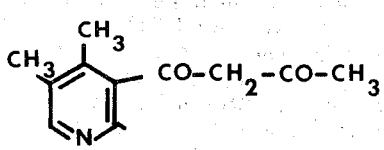

is obtained in 73% yield as yellowish crystals, melting point 46°–48° (from n-hexane).

EXAMPLE 6

3.5 g of 1-(2-methyl-5-pyridyl)-3-amino-n-butanol, 40 ml of ethanol (96% strength) and 6.0 g of 1-(4-n-butoxyphenoxy)-2,3-epoxy-propane (prepared from p-n-butoxyphenol and epichlorohydrin) are stirred for 20 hours at room temperature and then heated to 50° for 2 hours. Evaporation of the reaction mixture in vacuo gives 8.9 g of crude 1-(2-methyl-5-pyridyl)-3-(1-[p-n-butoxy-phenoxy]-2-hydroxypropyl(3)-amino)-butan-1-ol of the formula

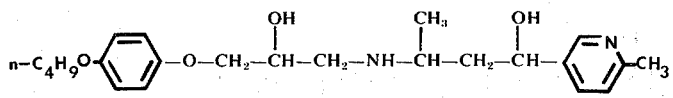

as an oil which is further purified by gel chromatography.

Analysis: ($C_{23}H_{34}N_2O_4$)
calculated: C 68.6 H 8.5 N 7.0 O 15.9
found: C 68.4 H 8.5 N 6.9 O 16.1

1-(2-Methyl-5-pyridyl)-3-amino-n-butanol can be used as the starting material, is obtained as follows: 20.0 g of (6-methyl-nicotinoyl)-acetone, 200 ml of ethanol and 0.5 g of ammonium bromide are saturated with ammonia at 50° and heated at 50° for 15 hours whilst continuing to introduce ammonia. 8.5 g of sodium boranate are introduced in portions over the course of 1 hour into the solution, obtained above, of 1-(2-methyl-5-pyridyl)-3-amino-but-2-en-1-one of the formula

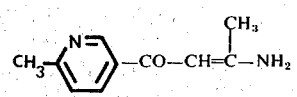

and the mixture is stirred for 7 hours at 70°. The solvent is distilled off in vacuo and the residue is taken up in 20% strength aqueous potassium hydroxide solution and pentanol-1. After working up in the usual manner, 19.2 g of crude 1-(2-methyl-5-pyridyl)-3-amino-n-butanol of the formula

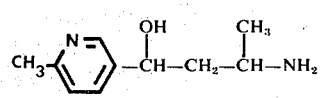

are obtained from the pentanol solution as an oil which can be purified further by column chromatography.

Analysis: ($C_{10}H_{16}N_2O$)
calculated: C 66.6 H 9.0 N 15.5 O 8.9
found: C 66.6 H 9.1 N 15.4 O 9.1

EXAMPLE 7

8.5 g of 1-(2-methyl-5-pyridyl)-3-chloro-butan-1-ol hydrochloride are introduced in small portions into a suspension of 7.3 g of 1-(4-n-butoxy-phenoxy)-3-amino-propan-2-ol (prepared from p-butoxy-phenol and epichlorohydrin, the reaction product then being reacted with ammonia) and 15.0 g. of anhydrous potassium hydroxide in 100 ml of anhydrous toluene. The mixture is stirred for 10 hours at room temperature and is additionally heated for 5 hours in a waterbath. After cooling, the salt is filtered off and the filtrate is stirred with water and sufficient hydrochloric acid to give a pH of 3 in the aqueous phase. The acid solution is separated from the toluene and washed with ethyl acetate; the mixture is then rendered alkaline with potassium hydroxide solution and is repeatedly extracted wit chloroform. Drying and evaporation of the chloroform solutiion gives 9.5 g of crude 1-(2-methyl-5-pyridyl)-3-(1-[p-n-butoxy-phenoxy]-2-hydroxypropyl(3)-amino)-butan-1-ol of the formula

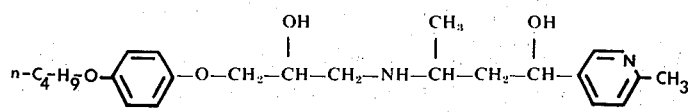

as an oil which is purified further by column chromatography.

Analysis: ($C_{23}H_{34}N_2O_4$)
calculated: C 68.6 H 8.5 N 7.0 O 15.9
found: C 68.7 H 8.5 N 6.8 O 16.0

1-(2-Methyl-5-pyridyl)-3-chloro-butan-1-ol hydrochloride, used as the starting material, is obtained as follows:

A suspension of the sodium salt of 6-methyl-nicotinoyl-acetone in anhydrous toluene is saturated with hydrogen chloride and then reacted with thionyl chloride in a known manner. Reduction of the reaction product gives 1-(2-methyl-5-pyridyl)-3-chloro-butan-1-ol hydrochloride which is used without additional purification

What we claim is:

1. Derivative of 1-phenoxy-3-amino-propan-2-ol having the formula

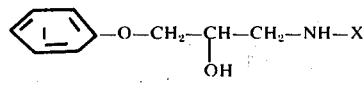

wherein X is selected from the group consisting of

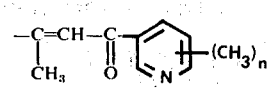

and

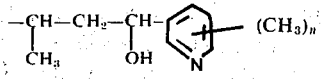

wherein $n$ is 1, 2 or 3 and the phenyl radical I can be monosubstituted, disubstituted or trisubstituted by alkyl having 1 to 4 carbon atoms, alkenyl or alkinyl having in either case up to 6 carbon atoms, cycloalkyl or cycloalkenyl having in either case a ring having 5 to 8 carbon atoms, alkoxy having up to 8 carbon atoms, alkenyloxy or alkinyloxy having in either case up to 5 carbon atoms, phenyl, chlorine or bromine, or the radical —$NR_1R_2$, wherein $R_1$ represents alkyl having 1 to 4 carbon atoms or aryl-substituted or alkyl-substituted carbonyl radical derived from an aromatic or aliphatic carboxilic acid having up to 11 carbon atoms, and $R_2$ represents hydrogen or alkyl having up to 4 carbon atoms, or a pharmaceutically acceptable acid addition salt of said derivative.

2. Derivative according to claim 1, wherein the phenyl radical I is substituted by a substituent selected from the group consisting of vinyl, allyl, methallyl and crotyl.

3. Derivative according to claim 1, wherein the phenyl radical I is substituted by cyclopentenyl.

4. Derivative according to claim 1, wherein the phenyl radical I is substituted by a radical selected from the group consisting of cyclopentyl and cyclohexyl.

5. Derivative according to claim 1, wherein the phenyl radical I is substituted by a substituent selected from the group consisting of methoxy, ethoxy, propoxy, isopropoxy, butoxy, n-pentyloxy, allyloxy, methallyloxy, propargyloxy and n-octyloxy.

6. Derivative according to claim 1, wherein the phenyl radical I is substituted by the radical —$NR_1R_2$, wherein $R_1$ is selected from the group consisting of methyl, ethyl, acetyl and benzoyl, and $R_2$ is selected from the group consisting of hydrogen, methyl and ethyl.

7. Derivative of 1-phenoxy-3-amino-propan-2-ol, having the structural formula

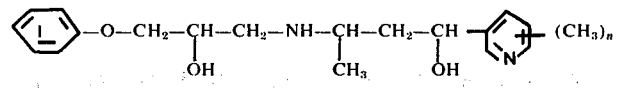

wherein, the nucleus I is selected from the group consisting of phenyl, chlorophenyl, bromophenyl, alkoxyphenyl having 1 to 8 carbon atoms in the alkoxy moiety, allyloxyphenyl, methallyloxyphenyl, benzyloxyphenyl and acetaminophenyl, and $n$ is 1, 2, or 3, and the pharmaceutically acceptable acid addition salts of said derivative.

8. The compound having the structural formula

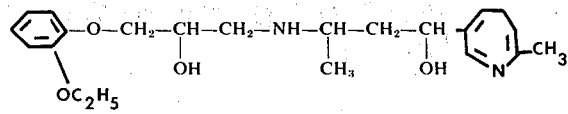

and the pharmaceutically acceptable acid addition salts of said derivative.

9. The compound having the structural formula

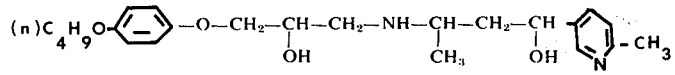

and the pharmaceutically acceptable acid addition salts of said derivative.

10. The compound having the structural formula

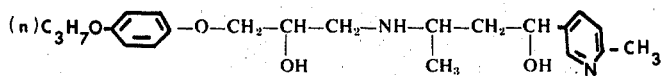

and the pharmaceutically acceptable acid addition salts of said derivative.

11. The compound having the structural formula

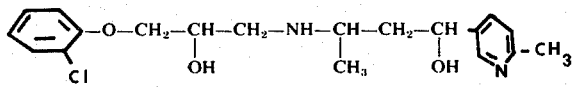

and the pharmaceutically acceptable acid addition salts of said derivative.

12. The compound having the structural formula

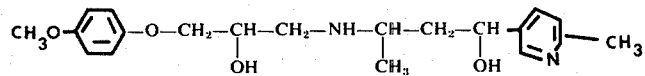

and the pharmaceutically acceptable acid addition salts of said derivative.

* * * * *

UNITED STATES PATENT OFFICE
CERTIFICATE OF CORRECTION

Patent No. 3,969,363     Dated July 13, 1976

Inventor(s) Raabe et al

It is certified that error appears in the above-identified patent and that said Letters Patent are hereby corrected as shown below:

Column 1, line 18, "C-CH" (in the formula) should read --C=CH--. Column 4, lines 18 (one occurrence) and 40 (two occurrences), "C-CH" should read --C=CH--; line 52, "  " should read --(CH$_3$)$_n$ ⇌ CH$_3$--.

Column 27, line 1, "C$_4$-H$_9$" should read --C$_4$H$_9$--; line 27, "  " should read --  --; line 50, the formula should read

 --. Column 28, line 42, the formula should read

 --; line 56, the formula should read --  --; line 66, the formula should read  --.

Column 29, line 7, the formula should read

 --; line 23, the formula

UNITED STATES PATENT OFFICE
CERTIFICATE OF CORRECTION

Patent No. 3,969,363     Dated July 13, 1976

Inventor(s) Raabe et al

It is certified that error appears in the above-identified patent and that said Letters Patent are hereby corrected as shown below:

should read -- 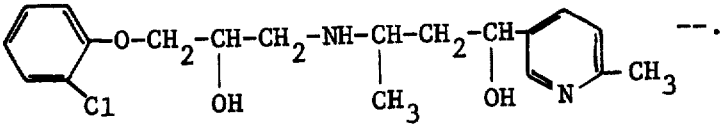 --. Column 30, line 13, the formula should read -- 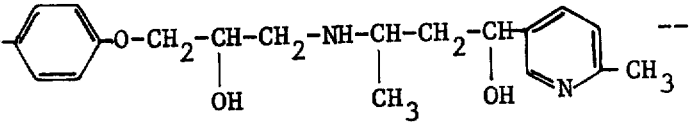 --.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*